United States Patent [19]
Yamamoto et al.

[11] Patent Number: 5,443,951
[45] Date of Patent: Aug. 22, 1995

[54] SPECIES-SPECIFIC OLIGONUCLEOTIDES FOR BIFIDOBACTERIA AND A METHOD OF DETECTION USING THE SAME

[75] Inventors: Takaharu Yamamoto; Masami Morotomi; Ryuichiro Tanaka, all of Tokyo, Japan

[73] Assignee: Kabushiki Kaisha Yakult Honsha, Tokyo, Japan

[21] Appl. No.: 93,884

[22] Filed: Jul. 20, 1993

[30] Foreign Application Priority Data

| | | |
|---|---|---|
| Jul. 20, 1992 [JP] | Japan | 4-192183 |
| Jul. 20, 1992 [JP] | Japan | 4-192184 |
| Oct. 2, 1992 [JP] | Japan | 4-287095 |
| Oct. 2, 1992 [JP] | Japan | 4-287097 |
| Oct. 2, 1992 [JP] | Japan | 4-287100 |

[51] Int. Cl.$^6$ .............................................. C12Q 1/68
[52] U.S. Cl. ..................... 435/6; 435/252.1; 536/24.32
[58] Field of Search ............... 435/6, 252.1; 536/24.32

[56] References Cited

U.S. PATENT DOCUMENTS 4,851,330  7/1989  Kohne ..................................... 435/6

FOREIGN PATENT DOCUMENTS 0272009  6/1988  European Pat. Off.
5-68595  3/1993  Japan.

OTHER PUBLICATIONS

Ludwig et al., International J. Systematic Bact., 42(1):161–165, Jan. 1992.
GenBank Database entries, Yang et al. Loci BIFR-RIGSI, BIFRRIGSO, BIFRRIGSA, BIFRRIGSC, BIFRRIGSK and BIFFRIGSN, Jan. 31, 1992.
Matthews et al., Analytical Biochemistry, 169:1–25, 1988.
Neefs et al., Nucleic Acids Res., 18 (Supplement); 2237–2317, 1990.
M. Salama et al., Applied and Environmental Microbiology, 57(5), pp. 1313–1318 (1991).
R. Amann et al., Letters to Nature, 351, pp. 161–164 (1991).
E. Jablonski et al., Nucleic Acids Research, 14, pp. 6115–6128 (1986).
T. Yamamoto et al., Applied and Environmental Microbiology, 58(12), pp. 4076–4079 (1992).
Y. Benno, BISEIBUTSU, 6(1), pp. 1–14 (1990).
Cotten et al., Development of a Bifidobacterium Adeloscentis-Specific DNA Probe, Abst. Gen. Meet. Am. Soc. Microbiol., 91(0):301 (1991).
Stackenbrandt et al., Partial 16S rNA Primary Structure of Five Acinomyces Species, Journal of General Microbiology, 136:37–43 (1990).
Yang et al., 16S Ribosomal RNA Phylogeny of Bifidobacteria, Abst. Annual. Am. Soc. Microbiol. 89, 89(0):282 (1989).

Primary Examiner—Margaret Parr
Assistant Examiner—Scott William Houtteman
Attorney, Agent, or Firm—Sughrue, Mion, Zinn, Macpeak & Seas

[57] ABSTRACT

Oligonucleotides which specifically hybridize to rRNAs of *Bifidobacterium infantis*, *Bifidobacterium bifidum*, *Bifidobacterium adolescentis*, *Bifidobacterium breve*, and *Bifidobacterium longum* represented by the sequences of formulae (I) to (V), respectively, or sequences complementary thereto:

| | |
|---|---|
| UAUCGGGGAGCAAGCGUGA | (I) SEQ ID NO: 1 |
| UCGGAUCGGAGCCUGC | (II) SEQ ID NO: 4 |
| CGCUUUUGACUGGGAGC | (III) SEQ ID NO: 7 |
| UGUGUUGAGUGUACCUU | (IV) SEQ ID NO: 10 |
| UAUCGGGGAGCAAGCGAGA | (V) SEQ ID NO: 13 | and a method of species-specifically detecting species of the genus Bifidobacterium of human origin comprising using these oligonucleotides as a labeled probe.

20 Claims, No Drawings

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Bifidobacterium infantis ( x i ) SEQUENCE DESCRIPTION: SEQ ID NO:1:

UAUCGGGGAG CAAGCGUGA                                            19

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( v i ) ORIGINAL SOURCE:
        ( A ) ORGANISM: Bifidobacterium infantis ( x i ) SEQUENCE DESCRIPTION: SEQ ID NO:2:

TCACGCTTGC TCCCCGATA                                            19

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Other nucleic acid (DNA complementary to cDNA)

( v i ) ORIGINAL SOURCE:
        ( A ) ORGANISM: Bifidobacterium infantis ( x i ) SEQUENCE DESCRIPTION: SEQ ID NO:3:

TATCGGGGAG CAAGCGTGA                                            19

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Bifidobacterium bifidum ( x i ) SEQUENCE DESCRIPTION: SEQ ID NO:4:

UCGGAUCGGA GCCUGC                                                                16

( 2 ) INFORMATION FOR SEQ ID NO:5:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA to rRNA ( v i ) ORIGINAL SOURCE:
        ( A ) ORGANISM: Bifidobacterium bifidum ( x i ) SEQUENCE DESCRIPTION: SEQ ID NO:5:

GCAGGCTCCG ATCCGA                                                                16

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: Other nucleic acid (DNA complementary to cDNA)

( v i ) ORIGINAL SOURCE:
        ( A ) ORGANISM: Bifidobacterium bifidum ( x i ) SEQUENCE DESCRIPTION: SEQ ID NO:6:

TCGGATCGGA GCCTGC                                                                16

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Bifidobacterium adolescentis ( x i ) SEQUENCE DESCRIPTION: SEQ ID NO:7:

CGCUUUUGAC UGGGAGC                                                               17

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( v i ) ORIGINAL SOURCE:
        ( A ) ORGANISM: Bifidobacterium adolescentis ( x i ) SEQUENCE DESCRIPTION: SEQ ID NO:8:

GCTCCCAGTC AAAAGCG                                                               17

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single ( D ) TOPOLOGY: linear ( i i ) MOLECULE TYPE: Other nucleic acid (DNA complementary to cDNA)

( v i ) ORIGINAL SOURCE:
    ( A ) ORGANISM: Bifidobacterium adolescentis ( x i ) SEQUENCE DESCRIPTION: SEQ ID NO:9:

CGCTTTTGAC TGGGAGC 17

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Bifidobacterium breve ( x i ) SEQUENCE DESCRIPTION: SEQ ID NO:10:

UGUGUUGAGU GUACCUU 17

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( v i ) ORIGINAL SOURCE:
        ( A ) ORGANISM: Bifidobacterium breve ( x i ) SEQUENCE DESCRIPTION: SEQ ID NO:11:

AAGGTACACT CAACACA 17

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid (DNA complementary to cDNA)

( v i ) ORIGINAL SOURCE:
        ( A ) ORGANISM: Bifidobacterium breve ( x i ) SEQUENCE DESCRIPTION: SEQ ID NO:12:

TGTGTTGAGT GTACCTT 17

( 2 ) INFORMATION FOR SEQ ID NO:13:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Bifidobacterium longum ( x i ) SEQUENCE DESCRIPTION: SEQ ID NO:13:

UAUCGGGGAG CAAGCGAGA 19

( 2 ) INFORMATION FOR SEQ ID NO:14:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( v i ) ORIGINAL SOURCE:
        ( A ) ORGANISM: Bifidobacterium longum ( x i ) SEQUENCE DESCRIPTION: SEQ ID NO:14:

```
TCTCGCTTGC TCCCCGATA                                              19
```

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Other nucleic acid (DNA complementary to cDNA)

( v i ) ORIGINAL SOURCE:
        ( A ) ORGANISM: Bifidobacterium longum ( x i ) SEQUENCE DESCRIPTION: SEQ ID NO:15:

```
TATCGGGGAG CAAGCGAGA                                              19
```

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO:16:

```
G W ATTACCGC GGCKGCTG                                             18
```

( 2 ) INFORMATION FOR SEQ ID NO:17:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Bifidobacterium infantis ( x i ) SEQUENCE DESCRIPTION: SEQ ID NO:17:

```
CUCUUUUAUC GGGGAGCAAG CGUG                                        24
```

( 2 ) INFORMATION FOR SEQ ID NO:18:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:

(A) ORGANISM: Bifidobacterium infantis (xi) SEQUENCE DESCRIPTION: SEQ ID NO:18:

AGUGAGUUUA CCCG                                                                                           14

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: Bifidobacterium adolescentis (xi) SEQUENCE DESCRIPTION: SEQ ID NO:19:

CGCUUUUGAC UGGGAGCAAC CUCGG                                                                               25

(2) INFORMATION FOR SEQ ID NO:20:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: Bifidobacterium adolescentis (xi) SEQUENCE DESCRIPTION: SEQ ID NO:20:

GGUGAGUGUA CCUU                                                                                           14

(2) INFORMATION FOR SEQ ID NO:21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: Bifidobacterium angulatum (xi) SEQUENCE DESCRIPTION: SEQ ID NO:21:

CGCUUUUGUU GGGGAGCAAG CUUCG                                                                               25

(2) INFORMATION FOR SEQ ID NO:22:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: Bifidobacterium angulatum (xi) SEQUENCE DESCRIPTION: SEQ ID NO:22:

GGUGAGUGUA CCUU                                                                                           14

(2) INFORMATION FOR SEQ ID NO:23:

(i) SEQUENCE CHARACTERISTICS:

( A ) LENGTH: 25 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Bifidobacterium bifidum ( x i ) SEQUENCE DESCRIPTION: SEQ ID NO:23:

CUCUUUUGUU UGGGAGCAAG CUUCG                    25

( 2 ) INFORMATION FOR SEQ ID NO:24:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Bifidobacterium bifidum ( x i ) SEQUENCE DESCRIPTION: SEQ ID NO:24:

GGUGAGUGUA CCUU                                14

( 2 ) INFORMATION FOR SEQ ID NO:25:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Bifidobacterium breve ( x i ) SEQUENCE DESCRIPTION: SEQ ID NO:25:

CUCUUUUGUU AGGGAGCAAG GCACUUUGU                29

( 2 ) INFORMATION FOR SEQ ID NO:26:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Bifidobacterium breve ( x i ) SEQUENCE DESCRIPTION: SEQ ID NO:26:

GUUGAGUGUA CCUU                                14

( 2 ) INFORMATION FOR SEQ ID NO:27:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Bifidobacterium dentium ( x i ) SEQUENCE DESCRIPTION: SEQ ID NO:27:

CGCUUUUGAU CGGGAGCAAC CUCGG                                                                25

( 2 ) INFORMATION FOR SEQ ID NO:28:

( i ) SEQUENCE CHARACTERISTICS:
     ( A ) LENGTH: 14 base pairs
     ( B ) TYPE: nucleic acid
     ( C ) STRANDEDNESS: single
     ( D ) TOPOLOGY: linear ( i i ) MOLECULE TYPE: rRNA ( v i ) ORIGINAL SOURCE:
     ( A ) ORGANISM: Bifidobacterium dentium ( x i ) SEQUENCE DESCRIPTION: SEQ ID NO:28:

GGUGAGUGUA CCCU                                                                            14

( 2 ) INFORMATION FOR SEQ ID NO:29:

( i ) SEQUENCE CHARACTERISTICS:
     ( A ) LENGTH: 24 base pairs
     ( B ) TYPE: nucleic acid
     ( C ) STRANDEDNESS: single
     ( D ) TOPOLOGY: linear ( i i ) MOLECULE TYPE: rRNA ( v i ) ORIGINAL SOURCE:
     ( A ) ORGANISM: Bifidobacterium longum ( x i ) SEQUENCE DESCRIPTION: SEQ ID NO:29:

CUCUUUUAUC GGGGAGCAAG CGAG                                                                 24

( 2 ) INFORMATION FOR SEQ ID NO:30:

( i ) SEQUENCE CHARACTERISTICS:
     ( A ) LENGTH: 14 base pairs
     ( B ) TYPE: nucleic acid
     ( C ) STRANDEDNESS: single
     ( D ) TOPOLOGY: linear ( i i ) MOLECULE TYPE: rRNA ( v i ) ORIGINAL SOURCE:
     ( A ) ORGANISM: Bifidobacterium longum ( x i ) SEQUENCE DESCRIPTION: SEQ ID NO:30:

AGUGAGUUUA CCCG                                                                            14

( 2 ) INFORMATION FOR SEQ ID NO:31:

( i ) SEQUENCE CHARACTERISTICS:
     ( A ) LENGTH: 47 base pairs
     ( B ) TYPE: nucleic acid
     ( C ) STRANDEDNESS: single
     ( D ) TOPOLOGY: linear ( i i ) MOLECULE TYPE: rRNA ( v i ) ORIGINAL SOURCE:
     ( A ) ORGANISM: Bifidobacterium pseudolongum ( x i ) SEQUENCE DESCRIPTION: SEQ ID NO:31:

CGCUUUUGUU CAAGGGCAAC ACGGUUUCGG CCGGUUGAGU GGAUUGU                                         47

( 2 ) INFORMATION FOR SEQ ID NO:32:

( i ) SEQUENCE CHARACTERISTICS:
     ( A ) LENGTH: 16 base pairs
     ( B ) TYPE: nucleic acid (C) STRANDEDNESS: single
        (D) TOPOLOGY: linear (i i) MOLECULE TYPE: rRNA (v i) ORIGINAL SOURCE:
        (A) ORGANISM: Bifidobacterium bifidum (x i) SEQUENCE DESCRIPTION: SEQ ID NO:32:

UCGGAUCGGA GCCUGC 16

(2) INFORMATION FOR SEQ ID NO:33:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (i i) MOLECULE TYPE: rRNA (v i) ORIGINAL SOURCE:
        (A) ORGANISM: Bifidobacterium adoloescentis (x i) SEQUENCE DESCRIPTION: SEQ ID NO:33:

UCGGAUUGGA GUCUGC 16

(2) INFORMATION FOR SEQ ID NO:34:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (i i) MOLECULE TYPE: rRNA (v i) ORIGINAL SOURCE:
        (A) ORGANISM: Bifidobacterium angulatum (x i) SEQUENCE DESCRIPTION: SEQ ID NO:34:

UCGGAUUGGA GUCUGC 16

(2) INFORMATION FOR SEQ ID NO:35:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (i i) MOLECULE TYPE: rRNA (v i) ORIGINAL SOURCE:
        (A) ORGANISM: Bifidobacterium animalis (x i) SEQUENCE DESCRIPTION: SEQ ID NO:35:

UCGGAUCGCA GUCUGC 16

(2) INFORMATION FOR SEQ ID NO:36:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (i i) MOLECULE TYPE: rRNA (v i) ORIGINAL SOURCE:
        (A) ORGANISM: Bifidobacterium breve (x i) SEQUENCE DESCRIPTION: SEQ ID NO:36:

UCGGAUCGCA GUCUGC                                                          16

(2) INFORMATION FOR SEQ ID NO:37:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: Bifidobacterium dentium (xi) SEQUENCE DESCRIPTION: SEQ ID NO:37:

UCGGAUUGGA GUCUGC                                                          16

(2) INFORMATION FOR SEQ ID NO:38:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: Bifidobacterium infantis (xi) SEQUENCE DESCRIPTION: SEQ ID NO:38:

UCGGAUCGCA GUCUGC                                                          16

(2) INFORMATION FOR SEQ ID NO:39:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: Bifidobacterium longum (xi) SEQUENCE DESCRIPTION: SEQ ID NO:39:

UCGGAUCGCA GUCUGC                                                          16

SPECIES-SPECIFIC OLIGONUCLEOTIDES FOR BIFIDOBACTERIA AND A METHOD OF DETECTION USING THE SAME

FIELD OF THE INVENTION

This invention relates to oligonucleotides having species specificity for various Bifidobacterium species, particularly those of human origin, and a species-specific method of detection using the same.

BACKGROUND OF THE INVENTION

Identification of species belonging to the genus Bifidobacterium has mainly been performed on the basis of phenotypic characteristics, such as carbohydrate fermentation patterns, gas-liquid chromatographic analyses of fatty acids, and cellular morphology. Recently, identification based on DNA-DNA homology has also been used (see Benno, Y., BISEIBUTSU, Vol. 6, pp. 1-12 (1990).

Identification based on phenotypic characteristics requires a high degree of skill and takes a period of time before an identification can be made. The DNA-DNA homology approach, which requires extraction of DNA from microbial cells, is disadvantageous in that bifidobacteria are gram-positive bacteria which require more complicated procedures for bacteriolysis than those needed with gram-negative bacteria. In addition, the values for DNA-DNA homology between closely related species with no distinct difference are high.

Hence, there has been keen demand for the development of a rapid, simple, and accurate method for detecting Bifidobacterium species, especially those found in humans, i.e., *Bifidobacterium infantis*, *B. bifidum*, *B. adolescentis*, *B. breve*, and *B. longum*.

SUMMARY OF THE INVENTION

In light of the demand for a better detection method, the present inventors have conducted extensive investigations. Studies were performed on detecting bifidobacteria using a labeled oligonucleotide having species specificity for a Bifidobacterium species as a probe and observing hybridization of the probe to the bacterium. This study was focused on the use of short oligonucleotides comprising about 20 bases, which would perform in situ hybridization without requiring extraction of nucleic acids, thereby making it feasible to detect even a 1-nucleotide difference.

Species-specific portions of 16S rRNAs were chosen as the target site for assays because the 16S rRNA sequences have recently been accepted as a highly reliable indication of phylogenetic classification and also because 16S rRNAs have a much higher copy number per cell than chromosomal DNA and are expected to exhibit increased detection sensitivity.

Standard strains of various bifidobacteria were subjected to enzymatic bacteriolysis, and crude high-molecular-weight RNAs were extracted by a conventional method. The 16S rRNA portion of the crude high-molecular weight RNA was partially sequenced according to a Sanger's [dideoxy chain termination] method using reverse transcriptase. After comparing the thus determined base sequences, it was found that the oligonucleotides having sequences represented by formulae (I) to (V) (SEQ ID NO:1, SEQ ID NO:4, SEQ ID NO:7, SEQ ID NO:10 and SEQ ID NO:13, respectively) shown below are specific to *Bifidobacterium infantis*, *B. bifidum*, *B. adolescentis*, *B. breve*, and *B. longum*, respectively, and are useful as primers for detecting bacteria in a polymerase chain reaction (PCR) method and that the oligonucleotides, when labeled, serve as a probe for species-specifically detecting bifidobacteria rapidly, simply, and accurately. The present invention has been completed based on these findings.

The present invention relates to (1) an oligonucleotide which specifically hybridizes to *Bifidobacterium infantis* rRNA which has a sequence represented by formula (I) (SEQ ID NO:1) or a sequence complementary thereto:

UAUCGGGGAGCAAGCGUGA (I)

(2) an oligonucleotide which specifically hybridizes to *Bifidobacterium bifidum* rRNA which has a sequence represented by formula (II) (SEQ ID NO:4) or a sequence complementary thereto:

UCGGAUCGGAGCCUGC (II)

(3) an oligonucleotide which specifically hybridizes to *Bifidobacterium adolescentis* rRNA which has a sequence represented by formula (III) (SEQ ID NO:7) or a sequence complementary thereto:

CGCUUUUGACUGGGAGC (III)

(4) an oligonucleotide which specifically hybridizes to *Bifidobacterium breve* rRNA which has a sequence represented by formula (IV) (SEQ ID NO:10) or a sequence complementary thereto:

UGUGUUGAGUGUACCUU (IV)

(5) an oligonucleotide which specifically hybridizes to *Bifidobacterium longum* rRNA which has a sequence represented by formula (V) (SEQ ID NO:13) or a sequence complementary thereto:

UAUCGGGGAGCAAGCGAGA (V)

and (6) a species-specific method for detecting various species of the genus Bifidobacterium found in humans comprising using these oligonucleotides as a labeled probe.

DETAILED DESCRIPTION OF THE INVENTION

The oligonucleotide specific to *Bifidobacterium infantis* has a sequence represented by formula (I) (SEQ ID NO:1) or a sequence complementary thereto represented by formula (I') (SEQ ID NO:2) or (I") (SEQ ID NO:3):

5' TCACGCTTGCTCCCCGATA 3' (I')

3' AGTGCGAACGAGGGGCTAT 5' (I")

The oligonucleotide specific to *Bifidobacterium bifidum* has a sequence represented by formula (II) (SEQ ID NO:4) or a sequence complementary thereto represented by formula (II') (SEQ ID NO:5) or (II") (SEQ ID NO:6):

5' GCAGGCTCCGATCCGA 3' (II')

3' CGTCCGAGGCTAGGCT 5' (II")

The oligonucleotide specific to *Bifidobacterium adolescentis* has a sequence represented by formula (III) (SEQ ID NO:7) or a sequence complementary thereto represented by formula (III') (SEQ ID NO:8) or (III") (SEQ ID NO:9):

5' GCTCCCAGTCAAAAGCG 3'   (III')

3' CGAGGGTCAGTTTTCGC 5'   (III")

The oligonucleotide specific to *Bifidobacterium breve* has a sequence represented by formula (IV) (SEQ ID NO:10) or a sequence complementary thereto represented by formula (IV') (SEQ ID NO:11) or (IV") (SEQ ID NO:12):

5' AAGGTACACTCAACACA 3'   (IV')

3' TTCCATGTGAGTTGTGT 5'   (IV")

The oligonucleotide specific to *Bifidobacterium longum* has a sequence represented by formula (V) (SEQ ID NO:13) or a sequence complementary thereto represented by formula (V') (SEQ ID NO:14) or (V") (SEQ ID NO:15):

5' TCTCGCTTGCTCCCCGATA 3'   (V')

3' AGAGCGAACGAGGGGCTAT 5'   (V")

Each of the above-described sequences may have additional based bonded to the 5'- or 3'-terminal thereof as long as it functions as a probe.

These oligonucleotides can be prepared by conventional chemical synthesis means, for example by an automated DNA synthesizer. DNA fragments containing the above-mentioned sequences can be prepared by enzymatic cleavage of genes from the corresponding Bifidobacterium species.

Species-specific detection of bifidobacteria using these oligonucleotides is carried out in a conventional manner using a labeled oligonucleotide as a probe. That is, any one of the species-specific probes is subjected to hybridization to a sample under assay, and the existence of a Bifidobacterium species corresponding to the probe is confirmed by examining whether or not hybrid cells are formed. Then, if desired, the same confirmations are successively made using the other oligonucleotide probes. The bifidobacteria found in humans present in the sample, i.e., *Bifidobacterium infantis, B. bifidum, B. adolescentis, B. breve,* and *B. longum,* can thus be detected with species specificity.

Labeled preparations are prepared by labeling the oligonucleotide with a detectable marker by conventional means. Labeling markers which may be used include radioisotopes, fluorescent substances, enzymes, biotin and hapten.

Hybridization between the labeled preparation and a sample can be performed in accordance with known techniques, such as dot blot hybridization and northern hybridization. The hybrid which are formed can be confirmed through the detection of the labeled preparation by known means, for example, autoradiography using radioisotopes, enzyme-labeled antibody techniques using enzyme or biotin, and the like.

Further, of these oligonucleotides, the DNA fragments represented by formulae (I') to (V') (SEQ ID NO:2, SEQ ID NO:5, SEQ ID NO:8, SEQ ID NO:11 and SEQ ID NO:14, respectively) and (I") to (V") (SEQ ID NO:3, SEQ ID NO:6, SEQ ID NO:9, SEQ ID NO:12 and SEQ ID NO:15, respectively) can be used as a primer in the PCR method for identification of species. More specifically, microbial cells to be identified are subjected to bacteriolysis, and any of the DNA fragments of formulas (I') to (V')(SEQ ID NO:2, SEQ ID NO:5, SEQ ID NO:8, SEQ ID NO:11 and SEQ ID NO:14, respectively) and (I") to (V")(SEQ ID NO:3, SEQ ID NO:6, SEQ ID NO:9, SEQ ID NO:12 and SEQ ID NO:15, respectively) is added thereto as a primer, followed by treatment with a DNA polymerase. If DNA amplification is observed using electrophoresis, etc., this means that the cells possess a gene portion which corresponds to the DNA fragment used, i.e., the cells are identified to be of the same species as the origin of the DNA fragment primer.

The present invention will now be illustrated in greater detail with reference to Examples, but it should be understood that the present invention is not construed as being limited thereto.

EXAMPLE 1

16S rRNA Sequence Determination (1) Cultivation and Preparation of Crude High-Molecular-Weight RNA The standard Bifidobacterium strain shown in Table 1 below were cultivated for one day in 100 ml of GAM broth (referred to the following formula, produced by Nissui Seiyaku Co., Ltd.) supplemented with 1% glucose. After incubation, the cells were collected by centrifugation, washed three times with a washing solution (50 mM Tris, 1 mM EDTA; pH=7.4) and suspended in 7.3 ml of the same washing solution. To the cell suspension were added 2.3 ml of 2M sucrose, 0.33 μl of 0.5 mg/ml M1 enzyme (N-acethylmuramidase, produced by Seikagaku Kogyo Co., Ltd.), and 0.07 ml of 50 mg/ml lysozyme, followed by incubating at 37° C. for 30 minutes for bacteriolysis. To the solution were added 925 μl of an EDTA solution (50 mM Tris, 250 mM EDTA; pH=8.0) and 575 μl of an SDS solution (20% sodium dodecylsulfate, 50 mM Tris, 20 mM EDTA; pH=8.0), followed by shaking at 60° C. until the mixture became clear. Deproteination of the solution was conducted using a TE solution (10 mM Tris, 1 mM EDTA; pH=7.4)-saturated phenol and then a 24:1 mixture of chloroform/isoamyl alcohol. Nucleic acids were then precipitated in ethanol.

The precipitate was dissolved in an adequate amount of a TE solution (10 mM Tris, 1 mM EDTA; pH=7.4), and an equal amount of 4M NaCl was added thereto, followed by allowing the resulting solution to stand on ice overnight to precipitate crude high-molecular-weight RNA. The high-molecular-weight RNA was collected by centrifugation, again dissolved in a TE solution, and ethanol precipitated to remove salts.

The resulting RNA was stored in 70% ethanol at −70° C. or was dissolved in a TE solution at an appropriate concentration.

| Formula of GAM broth (1 l) | |
|---|---|
| Peptone | 10.0 g |
| Soybean peptone | 3.0 g |
| Proteose peptone | 10.0 g |
| Digestive serum powder | 13.5 g |
| Yeast extract | 5.0 g |
| Heat extract | 2.2 g |
| Liver extract | 1.2 g |

| Formula of GAM broth (1 l) | |
| --- | --- |
| Glucose | 3.0 g |
| Potassium dihydrogenphosphate | 2.6 g |
| Sodium chloride | 3.0 g |
| Soluble starch | 5.0 g |
| L-cysteine hydrochloride | 0.3 g |
| Sodium thioglycolic acid | 0.3 g |
| pH 7.3 ± 0.1 | |

(3) Selection of Species-Specific Sequences for *Bifidobacterium infantis*, *B. bifidum*, *B. adolescentis*, *B. breve*, and *B. longum*

By comparing the sequences obtained in (2) above, partial sequences specific to *Bifidobacterium infantis*, *B. bifidum*, *B. adolescentis*, *B. breve*, and *B. longum* were selected. The partial sequences selected and the results of sequencing of other Bifidobacterium species are shown below.

```
         434   440        450                            482        491
          |     |          |                              |          |
B. inf.  CUCUUUUAUCGGGGAGCAAGCGUG                       AGUGAGUUUACCCG      (SEQ ID NO:17 and SEQ ID
                                                                             NO:18, respectively)
B. ado.  CGCUUUUGACUGGGAGCAACCUCGG                     GGUGAGUGUACCUU       (SEQ ID NO:19 and SEQ ID
                                                                             NO:20, respectively)
B. ang.  CGCUUUUGUUGGGGAGCAAGCUUCG                     GGUGAGUGUACCUU       (SEQ ID NO:21 and SEQ ID
                                                                             NO:22, respectively)
B. bif.  CUCUUUUGUUUGGGAGCAAGCUUCG                     GGUGAGUGUACCUU       (SEQ ID NO:23 and SEQ ID
                                                                             NO:24, respectively)
B. bre.  CUCUUUUGUUAGGGAGCAAGGCACUUUGU                 GUUGAGUGUACCUU       (SEQ ID NO:25 and SEQ ID
                                                                             NO:26, respectively)
B. den.  CGCUUUUGAUCGGGAGCAACCUCGG                     GGUGAGUGUACCCU       (SEQ ID NO:27 and SEQ ID
                                                                             NO:28, respectively)
B. lon.  CUCUUUUAUCGGGGAGCAAGCGAG                      AGUGAGUUUACCCG       (SEQ ID NO:29 and SEQ ID
                                                                             NO:30, respectively)
B. pse.  CGCUUUUGUUCAAGGGCAACACGGUUUCGGCCGGUUGAGUGGAUUGU                    (SEQ ID NO:31)

1302          1317      (SEQ ID NO:32)
          |             |
B. bif.  UCGGAUCGGAGCCUGC
B. ado.  UCGGAUUGGAGUCUGC         (SEQ ID NO:33)
B. ang.  UCGGAUUGGAGUCUGC         (SEQ ID NO:34)
B. ani.  UCGGAUCGCAGUCUGC         (SEQ ID NO:35)
B. bre.  UCGGAUCGCAGUCUGC         (SEQ ID NO:36)
B. den.  UCGGAUUGGAGUCUGC         (SEQ ID NO:37)
B. inf.  UCGGAUCGCAGUCUGC         (SEQ ID NO:38)
B. lon.  UCGGAUCGCAGUCUGC         (SEQ ID NO:39)
```

TABLE 1

| Species | Strain No. |
| --- | --- |
| B. adoloncentis | ATCC 15703 |
| B. bifidum | ATCC 29521 |
| B. breve | ATCC 15700 |
| B. infantis | ATCC 15697 |
| B. longum | ATCC 15707 |
| B. angulatum | ATCC 27535 |
| B. dentium | ATCC 27534 |
| B. pseudolongum | ATCC 25526 |

(2) Partial Sequence of 16S rRNA

The 16S rRNA was directly sequenced from RNA using AMV reverse transcriptase (RNA sequencing kit, produced by Boehringer Mannheim) according to a Sanger's dideoxy chain termination method. The universal primer [G(A or T)ATTACCGCGGC(G or T)GCTG] (SEQ ID NO:16) described in Lane et al., *Proc. Natl. Acd. Sci. USA*, Vol. 82, pp. 6955–6969 (1985) (hereinafter referred to as "PPR") was used as a primer for sequencing. The hybridization site of this primer corresponds to the position of from 519 to 536 of *E. coli* 16S rRNA.

In the sequencing, a mixture of 4 µl of a 2.0 mg/ml solution of the high-molecular-weight RNA prepared in (1) above, 1.5 µl of 20 µl/ml primer, and 1.5 µl of distilled water was used as an annealing solution. Electrophoresis of the reaction mixture was carried out using a 6% polyacrylamide gel containing 8M urea.

In the above sequences, the underlined region is a target site for the species-specific probe of the respective Bifidobacterium species. The numbers correspond to the positions from the 5'-terminal of the base sequence of the *E. coli* 16S rRNA (refer to Noller, H. F. and C. R. Woese, *Science*, Vol. 212, pp. 403–411 (1981)).

EXAMPLE 2

(1) Synthesis of Probe and Labeling

An oligonucleotide having a sequence complementary to each of the underlined species-specific sequences of the Bifidobacterium species shown in Example 1 was synthesized with a DNA synthesizer (Model 380B, produced by Applied Biosystems) and purified in the usual manner. The resulting oligonucleotides corresponding to *Bifidobacterium infantis*, *B. bifidum*, *B. adolescentis*, *B. breve*, and *B. longum* will hereinafter be referred to as probes "PIN", "PBI", "PAD", "PBR", and "PLO", respectively. These oligonucleotide probes and probe PPR (the Universal primer used for sequencing in Example 1-(2)) were 5'-end labeled with $^{32}P$ by using Megalabel (produced by Takara Shuzo Co., Ltd.).

(2) Dot Blotting of High-Molecular-Weight RNA to Membrane

An appropriate amount of a high-molecular-weight RNA from each of the microorganisms shown in Table 3 below was extracted in the same manner as in Example 1-(1), and the resulting extracts were dissolved in 10 µl of distilled water, and 20 µl of 100% formamide, 7 µl of formaldehyde, and 2 µl of 20×SSC (3M NaCl, 0.3M sodium citrate) were added thereto. The solution was incubated at 68° C. for 15 minutes to denature the RNA. A double amount of 20×SSC was added to the solution, and the resulting solution was applied to a nylon membrane (Gene Screen Plus, produced by E. I. Du Pont) set in a microfiltration apparatus (Bio-Dot, produced by Bio-Rad Laboratories). The membrane was dried at room temperature and heated at 80° C. for 30 minutes to remove formaldehyde.

(3) Hybridization

The resulting high-molecular-weight RNA-blotted membrane was soaked in 6×SSC (0.9M NaCl, 0.09M sodium citrate) and then put in a plastic bag. A prehybridization solution (6×SSC, 2×Denhardt's solution, 1% SDS, 0.1 mg/ml salmon sperm DNA, 10% dextran sulfate) was added thereto, followed by incubating at a temperature selected from 40° to 55° C., as shown in Table 2 below, for 1 hour. The prehybridization solution was replaced by a hybridization solution (6×SSC, 2×Denhardt's solution, 1% SDS, 10% dextran sulfate, about $10^6$ cpm labeled probe), and incubation was contained at the temperature shown in Table 2 for an additional period of 2 hours. The membrane was taken out of the bag and washed three times with 6×SSC at room temperature for 5 minutes each time. As a more stringent wash, the membrane was further washed at a temperature selected from 50° to 70° C., as shown in Table 2, for at least 30 minutes. Hybridization was examined by autoradiography or observation under a Betascope 603 blot analyzer (manufactured by Betagen Corp.).

TABLE 2

| | Treating Temperature (°C.) | | | | | |
|---|---|---|---|---|---|---|
| | PPR | PIN | PBI | PAD | PBR | PLO |
| Prehybridization and Hybridization | 55 | 55 | 55 | 50 | 40 | 55 |
| Washing | 65 | 70 | 65 | 60 | 50 | 70 |

The results of dot blot hybridization between each probe and each high-molecular-weight RNA are shown in Table 3.
+ ... Hybridization was observed.
− ... No hybridization was observed.

TABLE 3

| Species (Strain No.) | PPR | PIN | PBI | PAD | PBR | PLO |
|---|---|---|---|---|---|---|
| Escherichia coli (ATCC 11775) | + | − | − | − | − | − |
| Actinomyces israelii (ATCC 10048) | + | − | − | − | − | − |
| Enbacterium aerofaciens (ATCC 25986) | + | − | − | − | − | − |
| Peptostreptococcus productus (ATCC 27340) | + | − | − | − | − | − |
| Bifidobacterium adolescentis (ATCC 15703) | + | − | − | + | − | − |
| B. angulatum (ATCC 27535) | + | − | − | − | − | − |
| B. animalis (ATCC 25527) | + | − | − | − | − | − |
| B. bifidum (ATCC 29521) | + | − | + | − | − | − |
| B. breve (ATCC 15700) | + | − | − | − | + | − |
| B. dentium (ATCC 27534) | + | − | − | − | − | − |
| B. globosum | + | − | − | − | − | − |

TABLE 3-continued

| Species (Strain No.) | PPR | PIN | PBI | PAD | PBR | PLO |
|---|---|---|---|---|---|---|
| (ATCC 25864) | | | | | | |
| B. infantis (ATCC 15697) | + | + | − | − | − | − |
| B. longum (ATCC 15707) | + | − | − | − | − | + |
| B. pseudolongum (ATCC 25526) | + | − | − | − | − | − |

As is apparent from the results in Table 3, probe PPR hybridized to RNA from all of the strains tested. This accurately reflects the fact that the sequence of probe PPR is complementary to the common portion in the 16S rRNAs of all bacteria. Probe PPR is used as a positive control for detecting the presence of target RNAs for this very reason.

To the contrary, probe PIN hybridized to the RNA extracted from *B. infantis*, but not to those from other Bifidobacterium species or non-Bifidobacterium reference microorganisms including *Actinomyces israelii*, which is believed to be phylogenetically close to Bifidobacterium species. In other words, probe PIN was confirmed to be species-specific to *B. infantis*.

Likewise, probes PBI, PAD, PBR and PLO hybridized specifically to the RNA extracted from the respective target strains but not to those from other Bifidobacterium species or non-Bifidobacterium reference microorganisms, including *Actinomyces israelii*, which is believed phylogenetically close to Bifidobacterium species, and thus also proved specific to the respective species.

EXAMPLE 3

Dot blot hybridization was conducted between each probe and fixed cells of the microorganisms shown in Table 4 below.

(1) Cell Fixation with Formaldehyde

After having been cultured overnight, about 3 ml of microbial cells were collected by centrifugation, washed with a phosphate buffer (145 mM NaCl, 100 mM sodium phosphate; pH=7.4), and suspended in 5 ml of the same phosphate buffer. Formaldehyde was added thereto a concentration of 1%, and the mixture was left on ice for 30 minutes with occasional shaking. Centrifugal collection of the cells, followed by washing with a phosphate buffer were repeated twice, and the finally obtained cells were suspended in an adequate amount of a Tris buffer solution (145 mM NaCl, 10 mM Tris; pH=7.4).

(2) Dot Blot Hybridization

The fixed cells were applied to Gene Screen Plus set on Bio-Dot, and the membrane was heated at 80° C. for 1 hour. Hybridization was carried out in the same manner as in Example 2-(3).

The results observed are shown in Table 4, in which symbols + and − have the same meaning as in Table 3.

TABLE 4

| Species | Strain No. | PPR | PIN | PBI | PAD | PBR | PLO |
|---|---|---|---|---|---|---|---|
| *B. adolescentis* | ATCC15703 | + | − | − | + | − | − |
| " | NCDO 2229 | + | − | − | + | − | − |
| " | NCDO 2230 | + | − | − | + | − | − |
| " | NCDO 2231 | + | − | − | + | − | − |
| " | GO-27 | + | − | − | + | − | − |
| " | KO-14 | + | − | − | + | − | − |
| " | NA-19 | + | − | − | + | − | − |

TABLE 4-continued

| Species | Strain No. | PPR | PIN | PBI | PAD | PBR | PLO |
|---|---|---|---|---|---|---|---|
| B. bifidum | ATCC15696 | + | − | + | − | − | − |
| " | ATCC29521 | + | − | + | − | − | − |
| " | ATCC11863 | + | − | + | − | − | − |
| " | YIT 4070 (FERM P-11791) | + | − | + | − | − | − |
| " | YIT 4001 | + | − | + | − | − | − |
| " | YIT 4069 (FERM P-11788) | + | − | + | − | − | − |
| " | YIT 4007 (FERM BP-791) | + | − | + | − | − | − |
| B. breve | ATCC15700 | + | − | − | − | + | − |
| " | ATCC15698 | + | − | − | − | + | − |
| " | Ta-2 | + | − | − | − | + | − |
| " | Ka-6 | + | − | − | − | + | − |
| " | Ma-33 | + | − | − | − | + | − |
| " | YIT 4010 | + | − | − | − | + | − |
| " | YIT 4065 | + | − | − | − | + | − |
| B. infantis | ATCC15697 | + | + | − | − | − | − |
| Bifidobacterium infantis | ATCC15702 | + | + | − | − | − | − |
| " | ATCC25962 | + | + | − | − | − | − |
| " | P3-10 | + | + | − | − | − | − |
| " | P8-37-1 | + | + | − | − | − | − |
| " | P9-5 | + | + | − | − | − | − |
| " | P11-15 | + | + | − | − | − | − |
| B. longum | ATCC15707 | + | − | − | − | − | + |
| " | ATCC15708 | + | − | − | − | − | + |
| " | FERM P6548 | + | − | − | − | − | + |
| " | GO-8 | + | − | − | − | − | + |
| " | NA-2 | + | − | − | − | − | + |
| " | O-12 | + | − | − | − | − | + |
| " | YA-2 | + | − | − | − | − | + |
| B. angulatum | ATCC27535 | + | − | − | − | − | − |
| B. animalis | ATCC25527 | + | − | − | − | − | − |
| B. asteroides | ATCC25910 | + | − | + | − | − | − |
| B. catenulatum | ATCC27539 | + | − | − | − | − | − |
| B. dentium | ATCC27534 | + | − | − | − | − | − |
| B. globosum | ATCC25864 | + | − | − | − | − | − |
| B. indicum | ATCC25912 | + | − | + | − | − | − |
| B. pseudocatenulatum | JCM 1200 | + | − | − | − | − | − |
| B. pseudolongum | ATCC25526 | + | − | − | − | − | − |
| B. suis | ATCC27533 | + | + | − | − | − | − |
| B. thermophilum | ATCC25525 | + | − | + | − | − | − |
| B. thermophilum | ATCC25866 | + | − | + | − | − | − |
| Escherichia coli | ATCC11775 | + | − | − | − | − | − |
| Actinomyces israelii | ATCC10048 | + | − | − | − | − | − |
| Bacteroides ovatus | ATCC8483 | + | − | − | − | − | − |
| Bacteroides vulgatus | ATCC8424 | + | − | − | − | − | − |
| Enterococcus faecalis | ATCC19433 | + | − | − | − | − | − |
| Enterococcus faecium | ATCC8043 | + | − | − | − | − | − |
| Eubactecium aerofaciens | ATCC25986 | + | − | − | − | − | − |
| Eubactecium biforme | VPI9218 | + | − | − | − | − | − |
| Lactobacillus acidophilus | ATCC4356 | + | − | − | − | − | − |
| Lactobacillus casei | ATCC393 | + | − | − | − | − | − |
| Peptostreptococcus prevotii | ATCC9321 | + | − | − | − | − | − |
| Peptostreptococcus productus | ATCC27340 | | | | | | |
| Streptococcus lactis | YIT 2027 | + | − | − | − | − | − |
| Streptococcus thermophilus | ATCC19258 | + | − | − | − | − | − |

The results in Table 4 show hybridization of probe PPR to RNA from all of the cells tested, irrespective of the genus or species, similar to the results of Example 2, revealing that all the cells were sufficiently fixed.

To the contrary, probes PAD, PBR, and PLO hybridized exclusively with the corresponding species, irrespective of the strain sources, but not with any of the other species, tested. The probes PAD, PBR and PLO were thus proved specific to the respective species.

Probe PIN hybridized exclusively with the corresponding species, B. infantis, irrespective of the strain sources, but not with other species except Bifidobacterium suis, proving specific to B. infantis. Although probe PIN cross-reacted with the standard B. suis strain, because this species is only found in swine feces, such a cross-reaction is considered to be of no importance because B. suis would not be present the samples tested for Bifidobacterium infantis, such as foodstuffs or human feces.

Probe PBI hybridized exclusively with the corresponding species, B. bifidum, irrespective of the strain sources, but not with other species except for a few strains of other species, thus providing specific to B. bifidum. That is, although probe PBI showed hybridization with the standard strains of Bifidobacterium asteroides, B. indicum, and B. thermophilum, because these Bifidobacterium strains are of animal origin, such as bees, swine and cattle, such a cross-reaction is not considered to be important because these species would not be present in samples being tested for B. bifidum, such as foodstuffs or human feces.

The oligonucleotides according to the present invention are species-specific to Bifidobacterium bacteria found in humans, i.e., B. infantis, B. bifidum, B. adole-

*scentis*, *B. breve*, and *B. longum*, and are useful as probes for rapidly, simply and accurately detecting *Bifidobacterium* bacteria which are found in humans.

While the invention has been described in detail and with reference to specific examples thereof, it will be apparent to one skilled in the art that various changes and modifications can be made therein without departing from the spirit and scope thereof.

What is claimed is:

1. An oligonucleotide having the sequence of formula (I) or a sequence fully complementary to the sequence of formula (I):

5'-UAUCGGGGAGCAAGCGUGA-3'    (I)

SEQ ID NO:1.

2. The oligonucleotide as claimed in claim 1, wherein said sequence fully complementary to the sequence of formula (I) has the DNA sequence of formula (I') or a sequence fully complementary to the DNA sequence of formula (I'):

5'-TCACGCTTGCTCCCCGATA-3'    (I')

SEQ ID NO:2.

3. The oligonucleotide as claimed in claim 1, wherein said DNA sequence fully complementary to the sequence of formula (I') has the DNA sequence of formula (I''):

5'-TATCGGGGAGCAAGCGTGA-3'    (I'')

SEQ ID NO:3.

4. An oligonucleotide having the sequence of formula (II) or a sequence fully complementary to the sequence of formula (II):

5'-UCGGAUCGGAGCCUGC-3'    (II)

SEQ ID NO:4.

5. The oligonucleotide as claimed in claim 4, wherein said sequence fully complementary to the sequence of formula (II) has the DNA sequence of formula (II') or a sequence fully complementary to the DNA sequence of formula (II'):

5'-GCAGGCTCCGATCCGA-3' (II')

SEQ ID NO:5.

6. The oligonucleotide as claimed in claim 4, wherein said DNA sequence fully complementary to the sequence of formula (II') has the DNA sequence of formula (II''):

5'-TCGGATCGGAGCCTGC-3' (II'')

SEQ ID NO:6.

7. An oligonucleotide having the sequence of formula (III) or a sequence fully complementary to the sequence of formula (III):

5'-CGCUUUUGACUGGGAGC-3' (III)

SEQ ID NO:7.

8. The oligonucleotide as claimed in claim 7, wherein said sequence fully complementary to the sequence of formula (III) has the DNA sequence of formula (III') or a sequence fully complementary to the DNA sequence of formula (III'):

5'-GCTCCCAGTCAAAAGCG-3' (III')

SEQ ID NO:8.

9. The oligonucleotide as claimed in claim 7, wherein said DNA sequence fully complementary to the sequence of formula (III') has the DNA sequence of formula (III''):

5'-CGCTTTTGACTGGGAGC-3' (III'')
SEQ ID NO:9.

10. An oligonucleotide having the sequence of formula (IV) or a sequence fully complementary to the sequence of formula (IV):

5'-UGUGUUGAGUGUACCUU-3' (IV)

SEQ ID NO:10.

11. The oligonucleotide as claimed in claim 10, wherein said sequence fully complementary to the sequence of formula (IV) has the DNA sequence of formula (IV') or a DNA sequence fully complementary to the DNA sequence of formula (IV'):

5'-AAGGTACACTCAACACA-3' (IV')

SEQ ID NO:11.

12. The oligonucleotide as claimed in claim 10, wherein said DNA sequence fully complementary to the sequence of formula (IV') has the DNA sequence of formula (IV''):

5'-TGTGTTGAGTGTACCTT-3' (IV'')

SEQ ID NO:12.

13. An oligonucleotide having the sequence of formula (V) or a sequence fully complementary to the sequence of formula (V):

5'-UAUCGGGGAGCAAGCGAGA-3' (V)

SEQ ID NO:13.

14. The oligonucleotide as claimed in claim 13, wherein said sequence fully complementary to the sequence of formula (V) has the DNA sequence of formula (V') or a DNA sequence fully complementary to the DNA sequence of formula (V'):

5'-TCTCGCTTGCTCCCCGATA-3' (V')

SEQ ID NO:14.

15. The oligonucleotide as claimed in claim 13, wherein said DNA sequence fully complementary to the sequence of formula (V') has the DNA sequence of formula (V''):

5'-TATCGGGGAGCAAGCGAGA-3' (V'')

SEQ ID NO:15.

16. A method of detecting a specific species of the genus Bifidobacterium comprising the steps of:
(A) contacting a human sample containing unknown nucleic acids with an oligonucleotide probe in a hybridizing solution, wherein said probe is selected from the group consisting of:
(1) a labeled oligonucleotide having the sequence of formula (I):

5'-UAUCGGGGAGCAAGCGUGA-3' (I)

SEQ ID NO:1 or a sequence fully complementary to the DNA sequence of formula (I);
(2) a labeled oligonucleotide having the sequence of formula (II):

5'-UCGGAUCGGAGCCUGC-3' (II)

SEQ ID NO:4 or a sequence fully complementary to the DNA sequence of formula (II);
(3) a labeled oligonucleotide having the sequence of formula (III):

5'-CGCUUUUGACUGGGAGC-3' (III)

SEQ ID NO:7 or a sequence fully complementary to the DNA sequence of formula (III);
(4) a labeled oligonucleotide having the sequence of formula (IV):

5'-UGUGUUGAGUGUACCUU-3' (IV)

SEQ ID NO:10 or a sequence fully complementary to the DNA sequence of formula (IV); and (5) a labeled oligonucleotide having the sequence of formula (V):

5'-UAUCGGGGAGCAAGCGAGA-3' (V)

SEQ ID NO:13 or a sequence fully complementary to the DNA sequence of formula (V), and (B) determining whether said probe hybridizes to said unknown nucleic acids in said sample so as to detect whether said species of said genus is present in said sample, wherein when probe (1) hybridizes to said nucleic acids the species Bifidobacterium infantis is detected, wherein when said probe (2) hybridizes to said nucleic acids the species Bifidobacterium bifidum is detected, wherein when said probe (3) hybridizes to said nucleic acids the species Bifidobacterium adolescentis is detected, wherein when said probe (4) hybridizes to said nucleic acids the species Bifidobacterium breve is detected, and wherein when said probe (5) hybridizes to said nucleic acids the specimen Bifidobacterium longum is detected.

17. The method as claimed in claim 16, wherein said labeled oligonucleotide is an oligonucleotide labeled with a radioisotope.

18. The method as claimed in claim 16, wherein said labeled oligonucleotide is an oligonucleotide labeled with fluorescent molecules.

19. The method as claimed in claim 16, wherein said labeled oligonucleotide is an oligonucleotide labeled with an enzyme.

20. The method as claimed in claim 16, wherein said labeled oligonucleotide is an oligonucleotide labeled with a biotin.

* * * * *